United States Patent
Sava

(10) Patent No.: US 7,347,941 B2
(45) Date of Patent: Mar. 25, 2008

(54) TREATING MICRO-ORGANISMS IN WATER USING BORON CONDITIONED ENZYMES AND COMPOSITION THEREFOR

(75) Inventor: Alex Sava, New South Wales (AU)

(73) Assignee: Novapharm Research (Australia) Pty Ltd, Rosebery, New South Wales (AU)

( * ) Notice: Subject to any disclaimer, the term of this patent is extended or adjusted under 35 U.S.C. 154(b) by 429 days.

(21) Appl. No.: 10/519,583

(22) PCT Filed: Jun. 27, 2003

(86) PCT No.: PCT/AU03/00822

§ 371 (c)(1), (2), (4) Date: Dec. 27, 2004

(87) PCT Pub. No.: WO2004/002896

PCT Pub. Date: Jan. 8, 2004

(65) Prior Publication Data

US 2005/0242029 A1 Nov. 3, 2005

(30) Foreign Application Priority Data

Jun. 28, 2002 (AU) .......................... PS3280

(51) Int. Cl.
*C02F 3/00* (2006.01)
(52) U.S. Cl. .............. 210/606; 210/632; 210/764
(58) Field of Classification Search ............. 210/606, 210/632, 764
See application file for complete search history.

(56) References Cited

U.S. PATENT DOCUMENTS 6,093,522 A * 7/2000 Kitteridge ............ 430/432
6,864,196 B2 * 3/2005 Graham et al. ............ 442/59

FOREIGN PATENT DOCUMENTS

| FR | 2697645 | 10/1992 |
| WO | WO 96/21499 | 7/1996 |
| WO | WO 01/23534 A1 | 4/2001 |

OTHER PUBLICATIONS

Indian First Examination Report dated Jan. 3, 2006.

\* cited by examiner

*Primary Examiner*—Chester T. Barry
(74) *Attorney, Agent, or Firm*—Sonnenschein Nath & Rosenthal LLP

(57) ABSTRACT

The invention relates to methods and compositions for of treating water systems, particularly recirculating water systems contaminated by a biofilm containing sessile micro-organisms. The method includes the steps of forming a boron conditioned enzyme and contacting the biofilm with said boron conditioned enzyme, thereby planktonising the micro-organisms The boron conditioned enzyme retains a level of activity at least 40% of the initial activity of the unconditioned enzyme for at least two hours after contacting the biofilm, either in the presence or absence of a biocide or corrosion inhibitor which would normally deactivate the enzyme. In preferred embodiments a biocide is added with the conditioned enzyme. The method and compositions are also applicable to remediation of tepid water systems in which biofilm may harbour pathogens such as sessile *Legionella*.

41 Claims, No Drawings

TREATING MICRO-ORGANISMS IN WATER USING BORON CONDITIONED ENZYMES AND COMPOSITION THEREFOR

CROSS-REFERENCE TO RELATED APPLICATIONS

The present application is a national application based on PCT application PCT/AU03/00822, filed June 27, 2003, which claims priority to Australian application PS3280, filed June 28, 2002, which are incorporated herein by reference to the extend permitted by law.

TECHNICAL FIELD

This invention relates to systems for treating industrial waters, and especially to systems for treating recirculating water passing through air-conditioning systems, heat-exchangers, cooling towers or the like.

BACKGROUND ART

In air-conditioning systems such as are used, for example in hospitals, schools, office, apartment and other buildings it is common to pass recirculated water over the surfaces of evaporative coolers. Similar equipment is found in many processing plants including those in the chemical, paper, textile, mining and other industries.

Make-up water typically contains dissolved chemicals which become progressively more concentrated in the recirculating water due to evaporative losses. This is especially the case in air conditioning systems and cooling circuits. Corrosion of the plant including pumps, pipes, tanks, heat exchangers, evaporative coolers etc, is a major problem and commonly the pH of the water rises. The corrosion problem is usually addressed by the addition of various water treatment chemicals. The present state of the corrosion inhibition art is summarised by Hartwick, D. in ASHRAE Journal, Feb. 2001. The primary corrosion Inhibitors may be classified as being (1) reducing Agents, (2) oxidizing agents, or (3) film formers. Reducing agents are rarely used nowadays because of their drawbacks. Oxidizing agents (e.g. chromate, molybdate, nitrite) react directly with the metal surface. While chromate and molybdate are effective, they are now seldom used because of environmental and health concerns and in many States their use is banned. Nitrite in too low a concentration can cause severe pitting, and too little nitrite is worse than none at all because it will speed up the corrosion process. Exposure of nitrite to bacteria has the potential to oxidize nitrite to nitrate or reduce it to ammonia both of which can reduce the nitrite concentration with deleterious results. Attempting to control biological activity with oxidizing biocides will oxidize the nitrite to nitrate and the efficacy of non-oxidizing biocides tends to be less certain. Consequently use of nitrites has fallen into disfavour. Among the film formers ortho-phosphate and organic phosphonates are the most common inhibitors. They act by forming a protective film on metal surfaces, but suffers from a tendency to precipitate with metal ions or hardness salts in the bulk water.

A second problem arises from the existence of slimes, bio-film, bacteria and fungi in waters. Slime and bio-film reduce pump efficiency and may seriously interfere with flow rates. In addition slimes reduce heat transfer across heat exchange surfaces, blind filters, and plug nozzles. The presence of slime and bio-film promotes corrosion because sessile bacteria in the slime or bio-film release acids and because the slime and bio-film adsorb and reduce the effectiveness of other water treatment chemicals. The term "slime" refers to a broad range of mucous, viscous, and leathery materials. These materials typically comprise or originate from polymeric, generally polysaccharide excretions produced by a broad spectrum of micro-organisms. In the past and up to the present biological deposits of all types including slime and bio-film are treated by the addition of biocides. Where slime and bio-film are present, biocides are frequently added in an effort to destroy the bacteria or microflora population which may produce the slimes. Chemicals which are used for this purpose included chlorine compounds such as chlorophenates; organomercurial compounds such as phenylmercuric acids; thiocarbamate compounds; thiocyanate compounds such as the isothiocyanates and methylene-bis-thiocyanate (MBT); tributyltin oxide; and the like. However, these chemicals are costly and highly toxic in the quantities known to be required for effective control of microbial populations. The possibility of their release into the environment is unacceptable, and their removal from water prior to disposal is uneconomical and poses risks of environmental pollution. Environment and occupational health and safety regulations now prevent the use of many such biocides in water treatment systems. Additionally, it appears that no precise correlation exists between the size of the bacterial population and the accumulation of slime or bio-film. Substantial slime accumulations have been observed even in waters having a low bacterial count. Similarly, high bacterial counts have been observed in waters having no significant slime accumulation. Consequently, use of a biocide may not adequately control biological slime or bio-film accumulations.

A further problem arises from the presence of planktonic bacteria in air-conditioning and some other systems, and especially from bacteria harmful to humans such as *Legionella*. First discovered in 1976, *Legionella* has the unusual characteristic of causing two diseases—Legionnaires disease and Pontiac Fever. Legionnaires disease is a pneumonia which affects 2-5% of those exposed. Between 5-15% of those who contract the disease die from it. Pontiac Fever attacks 95% of those exposed. Planktonic bacteria exist as a suspension in the bulk water. Planktonic *Legionella* bacteria may be carried by air bome spray particles from the system. *Legionella pneumophilia* bacteria are pathogenic when inhaled after the water in which they are resident becomes atomised. They may infect, or indeed ultimately kill, persons in the vicinity. It is therefore important to keep bacterial levels below acceptable limits. No biocide at a level safe to use in an air-conditioning system is effective to kill both sessile and planktonic *Legionella* in an operating system.

*Legionella* breeds in bio-film and slime and it is widely believed that that the best means of control is to close down a plant periodically for removal of the slime and bio-film eg by physical scrubbing and then treating with sodium hypochlorite to disinfect its surfaces. In fact, the Law in the State of New South Wales requires such action in water cooling towers at intervals of no longer than 3 months, and many other states have, or propose, similar legislation.

In the last decade, as an alternative to treatment with biocides, it has been proposed that slime and bio-film accumulation be controlled by use of enzymes. The various proposals for slime and bio-film control using one or more enzymes can be classified into two main groups. The first group consists of enzyme treatments including one or more protease enzymes, and the second to enzyme systems having one or more enzymes but not including a protease. The enzymes specifically attack the slime layer surrounding sessile bacteria but have little effect on planktonic Bacteria. Much of the work conducted with enzymes has been directed primarily at paper production where conditions are excellent for growing slime and bio-film, where the damage to production from slime and bio-film is costly, and where corrosion is a relatively minor problem so that other water treatment chemicals are not a complicating factor. The emphasis in such systems is on slime and bio-film elimination. Bacteria are only a problem in paper making insofar as they produce more slime, and as there is no correlation of slime production with the presence of planktonic bacteria, it is sufficient to prevent sessile micro-organism multiplication.

In contrast, the present inventor has found have found that in cooling towers the presence of an enzyme can result in an increase in planktonic *Legionella* concentration. It is believed this is partly because the enzyme physically releases micro-organisms trapped in the bio-film, and also partly because a large number of *Legionella* organisms may be engulfed within protozoa and thereby protected from the enzyme while the protozoa is released from the slime or bio-film . Experiments have shown that some species of *Legionella* can multiply intra-cellularly within certain free living protozoa. This may well be a hitherto unrecognised problem in paper mills and possibly elsewhere.

A similar problem to that occurring in recirculating water systems occurs in tepid water systems such as are found in hospitals, nursing homes, schools, jails and hotels to provide "hot" water at a "safe" temperature to showers, wash-basins or in spa baths. For almost thirty years it has been known that *Legionella* species can colonise such tepid water systems. *Legionella* species have adapted themselves to survive temperatures of up to approximately 55° C., conditions which kill many competing organisms. *Legionella pneumophilia* bacteria are pathogenic. At least one death has been attributed to infection with *Legionella* contracted from inhalation of the water spray of a shower in a hospital tepid water system. Hitherto the only treatment recommended for tepid water systems has been to periodically flush with sodium hypochlorite. The present inventors have found that chlorine treatment is ineffective against sessile *Legionella* harboured in a biofilm in the interior of a tepid water system.

Any discussion of the prior art throughout the specification should in no way be considered as an admission of the state of the common general knowledge in the field. Although the present invention is discussed with particular reference to *Legionella* it will be understood that similar considerations apply to many other micro-organisms including other harmful bacteria, fungi, moulds, etc. In water treatment systems the bacteria of general concern are gram positive.

It has also been proposed to treat water with a combination of an enzyme and a biocide. U.S. Pat. No. 4,684,469 (Pederson) describes a method to increase the antimicrobial activity of a biocide in an industrial water stream in which a selected biocide is combined with a polysaccharide degrading enzyme. Pederson used enzymes generated in-situ by bacterial cultures which are themselves pathogenic and unsuitable for use in industrial water systems. His preferred biocides are MBT and dithiocarbamates both of which are undesirable from an environmental and occupational health viewpoint. The preferred enzyme is a levan hydrolase. Pederson requires that the concentration of enzyme be monitored to maintain a concentration of at least 2 ppm of a preparation having an activity of at least 500 u/ml. However monitoring can not be done automatically and requires time consuming and labour intensive laboratory analysis. The examples given by Pederson show that under laboratory conditions the enzyme alone has substantially zero (or a negative) effect on microbial colony formation. When biocide was added half an hour after enzyme addition, the reduction in colony formation of the combination was greater than the reduction obtained by the biocide alone by a factor of 3 log or 4 log. U.S. Pat. No. 5,324,432 (Robertson) noted that Levan Hydrolase had no effect on sheathed micro-organisms such as are found in paper mill systems and proposed to treat with a protease and a biocide. The preferred combination is DBNPA and trypsin. The only example given is "contemplative" and involves treatment of the water with enzymes for 1-15 minutes followed by addition of hypochlorite.

These proposals prefer to add the biocide separately from, and subsequently to, addition of an enzyme to the paper-making machine's water stream. However simultaneous separate addition was considered feasible.

The present applicant has found combinations of biocide/enzyme as proposed in the prior art are not effective in cooling towers. At first it was hypothesized that this may be due to deactivation of the enzymes by the biocides. The present inventor has found that in systems of the kind described by Pederson and Robertson the enzyme is virtually ineffective within two hours of addition of the biocide. Thus even in a favourable case the enzyme must be added continuously or repetitively at short (less than 2 hour, preferably less than 30 min) intervals. This renders the system impracticable because of the difficulty of monitoring enzyme activity in a cooling tower environment and because of the low effectiveness and high cost over time. However the present inventor has also found that in the presence of corrosion inhibitors, this problem of enzyme denaturation is greatly exacerbated making use of enzyme/biocide combinations impractical in cooling towers and too expensive to be considered.

In summary, the present inventor has found that corrosion inhibitors in practical use in cooling towers nowadays de-activate enzymes either via direct oxidation or via surface absorption. In addition, enzymes are not compatible with most biocides which absorb onto enzyme proteins thus effectively deactivating enzymatic activity. Although some enzyme manufacturers claim that enzyme maintain their activity in a chlorine environment, the claim relates to laundry conditions and exposure times of around 10-15 minutes, as opposed to at least 24 hours as required for cooling tower maintenance.

To date no treatment has proved to be capable of avoiding the need for closure of cooling towers at 3 monthly intervals for cleaning. Enzymes are not effective in systems treated with preferred modern primary corrosion inhibitors (i.e. oxidizing agents or film formers). Biocides, at levels deemed safe to use, are not effective because they cannot penetrate through bio-film and attack *Legionella* in the bio-film or the *Legionella* that is parasitic within protozoa. Moreover, biocides are unable to kill both sessile and planktonic bacteria at levels of biocide considered safe. Combinations of enzymes and biocides result in each deactivating the other and have been found to be ineffective in the presence of modern corrosion inhibitors which rapidly deactivate enzymes.

No enzyme system, biocide, or enzyme/biocide combination from the prior art has been found which simultaneously meets the requirements for:

(1) compatibility with corrosion inhibitors, (2) environmental acceptability, (3) health and safety acceptability, (4) ability to control bio-film containing *Legionella* and ability to control planktonic *Legionella* sufficiently so that closure of the plant for cleaning at three monthly intervals can be avoided.

In addition, in the prior art when an enzyme and a biocide have been combined it has usually been necessary to add them separately. That is because the biocides have tended deactivate the enzymes or the enzymes to deactivate the biocides. This separation necessitates duplication of pumps, storage and feed tanks, as well as ancillary equipment for stirring, feed control and the like. It would be very advantageous to provide a water treatment composition which met all the requirements for treating water in an air-conditioning system or any other bulk water system and which could be combined in or delivered from a single container or tank. More preferably the combination would be available as a storage stable composition or concentrate.

It is an object of the invention to provide a method of treatment of industrial recirculating water which avoids or ameliorates at least some of the above discussed disadvantages of prior art. It is an object of preferred embodiments of the invention to provide a method and composition which will avoid the need for plant closure, or at least prolong the period in which the plant can be safely operated without closure for cleaning.

It is a further object to provide a method and composition for remediation of tepid water systems in which a biofilm harbours micro-organisms, such as for example, Legionella.

DESCRIPTION OF THE INVENTION

According to a first aspect, the invention provides a method of treating sessile micro-organisms in a biofilm in a water system, said method including the steps of: addition to the system at least one enzyme having an initial activity in water; conditioning said enzyme with a boron compound to form a boron conditioned enzyme; said boron compound being added in a concentration sufficient that the boron conditioned enzyme retains a level of activity at least 40% of said initial activity for at least two hours after said addition.

According to a second aspect, the invention provides a method of planktonising sessile micro-organisms in a biofilm said method including the steps of: adding at least one enzyme to a water system in contact with the biofilm, said enzyme being conditioning with a boron compound to form a boron conditioned enzyme; the boron compound being added in a concentration sufficient that the boron conditioned enzyme retains a level of activity at least 40% of its initial activity for at least two hours after said contacting, and wherein the enzyme is selected to be of a kind and in a concentration sufficient to planktonise said sessile microorganisms; and wherein said enzyme and said boron compound are synergistically effective in combination.

More particularly, the invention provides a method of treatment of a recirculating water system containing an oxidizing or film forming corrosion inhibitor, said method including the steps of adding one or more enzymes at an initial level of activity to the system; each of said enzymes having been conditioned with a sufficient concentration of a boron compound to maintain its activity at greater than 40% of the initial level in the presence of the corrosion inhibitor for more than 2 hours after the enzyme addition, and adding one or more biocides to the system.

In preferred embodiments of the invention sufficient boron compound is added so as to maintain the activity of the one or more enzymes in the presence of the corrosion inhibitor at greater than about 40% of the initial level for more than 4 hrs, and more preferably for longer than 8 hrs. Highly preferred embodiments maintain the activity of the enzyme at greater than 40% of the initial activity for longer than 12 hours. In some cases activity of greater than 75% and as much as 100% has been retained after 24 hrs.

Preferably, the method further includes the step of adding at least one biocide; and wherein said boron conditioned enzyme retains a level of activity at least 40% of said initial activity for at least two hours after addition.

The method of the present invention maybe particularly suited for those cases where the biofilm is in a recirculating water system. It is also suitable for use where the biofilm is in a non circulating tepid water system.

Preferably, the boron conditioned enzyme retains at least 40% of the initial activity of said enzyme for at least 12 hours and even more preferably the boron conditioned enzyme retains at least 75% of the initial activity of said enzyme for at least 24 hours.

It is important to note that the boron conditioned enzyme may be formed by contacting said enzyme and said boron compound prior to their addition to water (preconditioned), or alternatively the boron conditioned enzyme is formed by contacting said enzyme with said boron compound in water.

It is preferred that the boron conditioned enzyme and said biocide are added together, substantially simultaneously, or separately in an alternative preferred embodiment, the enzyme, the boron containing compound and the biocide are added together, substantially simultaneously or separately, and in any order.

Preferably the enzyme is selected from the group consisting of proteases, carbohydrases, esterases, hydrazes, amylases, catalases, lipases, cellulases, peroxidases, invertases, levanbiohydrolases and mixtures thereof. Most preferably, the enzyme is a protease, an amylase or a mixture thereof. in one preferred embodiment, the enzyme is a protease employed at an activity of 5E-4 to 10E-3Au/g, more preferably 1E-3 to 3E-3Au/g and most preferably about 2.5E-3Au/g. In another preferred embodiment, the enzyme is an amylase employed in a concentration equivalent to 10 to 1000 Nu/g, more preferably 100-500 Nu/g and most preferably about 300 Nu/g.

It is desirable that the enzyme be combined with the boron compound prior to addition to water containing a corrosion inhibitor, or shortly thereafter. Without wishing to be bound by theory, the boron compound apparently preconditions the enzyme so as to protect it from denaturation. Boron compounds are sometimes herein referred to as "boron" for simplicity.

Preferably the boron compound is selected from borax, boric acid, boric oxides, ortho-borates, meta-borates pyroborates, perborates, boronic acids or mixtures thereof. Preferably the ratio of weight of boron to weight of enzyme (as dried protein) is in the range 3:1 to 3:10. Preferably the boron compound is present in a concentration of 0.01 to 10%, more preferably 0.1 to 10% Preferably, the biocide is selected from thiazole/imidazole biocides, nitroparaffin biocides, thiadiazines, dithiocarbamates, thiocyanates or quaternary ammonium chlorides or their mixtures thereof, and is preferably employed in a concentration of from 0.1 to 1000 ppm, more preferably 1 to 150 ppm, most preferably 10 to 50 ppm. The biocide is preferably of a kind and in a concentration which is environmentally acceptable, and which in combination with the enzyme is effective to prevent growth of Legionella micro-organisms in the system. Highly preferred biocides are selected from thiazolelimidazole biocides (particularly isothiazolin derivatives) and nitroparaffin biocides (such as 2-bromo-2-nitropropane-1,3 diol).

In preferred embodiments water includes one or more corrosion inhibitors, such as an oxidising corrosion inhibitor or a film forming corrosion inhibitor.

Preferably the enzymes are added at a rate to maintain an effective activity in the recirculating water over at least 12 hours and the biocide is selected to maintain combined planktonic and sessile bacteria at below 1000, and more desirably at below 10 cfu per ml.

Preferably, the planktonic and sessile bacteria in total in said water are maintained at below 1000 cfu/ml, and more preferably below 10 cfu/ml.

Preferably, the biocide in combination with said boron conditioned enzyme is effective in reducing growth of organisms selected from the group consisting of Legionella micro-organisms, Aerobacter levanlcum, Pseudomonas aeruginosa, Rhodoturula glutinis yeasts, Bacillus subtilis. Most preferably the biocide in combination with said boron conditioned enzyme is effective in reducing growth of Legionella micro-organisms in the system.

Preferred methods according to the invention were found to protect enzymes from corrosion inhibitor deactivation for a extended period (up to 24 hrs).

According to a third aspect the invention provides a method of treatment of water including the steps of:

providing at least one enzyme having an initial activity in water;

conditioning said enzyme with a sufficient concentration of a boron compound to produce a boron conditioned enzyme;

adding at least one biocide and wherein when said boron conditioned enzyme is in contact with said water it retains a level of activity at least 40% of said initial activity for at least two hours after contacting said water; and wherein said enzyme and said biocide are synergistically effective in combination.

According to a fourth aspect the invention provides a method of remediating a tepid water system harbouring Legionella including the steps of treating the system with at least one enzyme having an initial activity in water;

conditioning said enzyme with a sufficient concentration of a boron compound to produce a boron conditioned enzyme; and wherein when said boron conditioned enzyme is in contact with said water it retains a level of activity at least 40% of said initial activity for at least two hours after contacting said water; and wherein said enzyme and said boron compound are synergistically effective in combination.

Preferably the tepid water is between 40 and 55° C., and more preferably between 45 and 50° C.

According to a sixth aspect the invention provides a composition for treating water including:
  at least one enzyme having an initial activity;
  a sufficient amount of a boron compound to condition and stabilise said enzyme so as to form a boron conditioned enzyme. said boron conditioned enzyme retaining at least 40% of said initial activity for at least two hours after contacting said water; and
  at least one biocide.

In certain embodiments, the invention provides a composition including in combination one or more enzymes, one or more biocides, and sufficient boron compound to precondition and stabilize said one or more enzymes so as to maintain at least 40% of its initial activity after 2 hours when added to water containing up to a predetermined concentration of an oxidizing or a film forming corrosion inhibitor.

The boron conditioned enzyme and biocide may be added together or separately and continuously or intermittently. However it is strongly preferred that the boron conditioned enzyme, and biocide are added substantially simultaneously. More preferably they are added together in combination by making up a solution from a composition according to the second aspect. in practice of the invention the addition may be continuous or repeated at short intervals but for preference is repeated at long time intervals e.g. at 8, 12, or 24 hour intervals. If desired the composition may also include selected corrosion inhibitors.

The present applicant has found that unprotected enzymes are deactivated within about one hour by both biocides and by corrosion inhibitors. For example the present inventor has found that a protease when combined with a biocide such as 2,2-dibromo-3-nitriloproionamide (DBNPA) retains less than 5% of its activity after 1 hour in an industrial recirculating water system containing modem corrosion inhibitors. The present inventor has also found, on the other hand, that biocides at concentrations which are environmentally and otherwise safe to use, only become fully effective after several hours and may require 12 hours in the presence of an active enzyme to be effective. If the enzyme can be sufficiently stabilized to retain greater than 50% of its activity for say 8 or 12, hours, then the combination is astonishingly effective in comparison with prior art in systems containing corrosion inhibitors.

Preferably the enzyme is selected from a group consisting of proteases, carbohydrases, esterases, hydrazes, amylases, catalases, lipases, cellulases, peroxidases, invertases, levanbiohydrolases and mixtures thereof. More preferably the enzyme is a protease, an amylase or mixtures thereof.

For preference the enzyme is one or more enzymes selected from the group consisting of selected from the group consisting of proteases, carbohydrases, esterases, hydrazes, amylases, catalases, lipases, amylases, cellulases, peroxidases, invertases, and mixtures thereof.

Preferably the protease is employed in a concentration sufficient to provide an activity of 5E-4 to 10E-3Au/g in use, more preferably 1E-3 to 3E-3Au/g in use and most preferably about 2.5E-3Au/g in use. Preferably, amylase is employed in a concentration sufficient to provide an activity of 10 to 1000 Nu/g in use, more preferably 100-500 Nu/g in use and most preferably about 300 Nu/g in use.

Preferably, the boron compound is selected from borax boric acid, boric oxides, orthoborates, meta borates or pyroborates, perborates boronic acids or mixtures thereof, preferably in a concentration of 0.1 to 10%.

While boron compounds have previously been added to enzymes to prevent autoproteolytic activity and to stabilize enzymes against deterioration in transit and storage they have not hitherto been combined with an enzyme in a concentration selected to protect the enzyme against the effect of corrosion inhibitors, or biocides, or for the purpose of maintaining the activity of the enzyme over time in the presence of those agents. Suitable boron compounds are boric acid, boric oxide, sodium ortho-, meta-, or pyro-borate and perborates. As will be appreciated by those skilled in the art, boron has previously been combined with enzymes in small concentrations to protect an enzyme from autolysis or to act as a preservative during storage and shipment but it has not been practiced to pre-treat an enzyme with a boron compound in a concentration selected to protect the enzyme from loss of activity in the presence of corrosion inhibitors or the like.

In preferred embodiments of the invention the efficacy of the boron compound is enhanced by addition of a suitable solvent such as a polyol or other micelle immiscible solvent.

In preferred embodiment, a polyol solvent is added to said boron compound. The polyol solvent is preferably selected from glycerol, propylene glycol, mixtures of glycerol and propylene glycol, and other micelle immiscible solvents.

The biocide is preferably selected from thiazole/imidazole biocides, nitroparaffin biocides, thiadiazines, dithiocarbamates, thiocyanates, quaternary ammonium chlorides or their mixtures thereof. Preferably the biocide is employed in a concentration of from 0.1 to 10%, more preferably 1 to 10%.

As stated above highly preferred biocides for use in the invention are selected from thiazole/imidazole biocides (particularly isothiazalin derivatives) and nitroparaffin biocides (particularly 2-bromo-2-nitropropane-1,3 diol).

Other biocides which may be useful include, without limitation,:

Thiadiazines such as 3,5-dimethyl-tetrahydro-2H-1,3,5-thiadiazine-2-thione;

dithiocarbamates such as sodium dimethyl dithiocarbamate;

disodium ethylene bis(dithiocarbamate);

Thiocyanates such as methylene bis-thiocyanate;

Quaternary ammonium chlorides such as alkyl dimethyl benzyl ammonium chloride;

dialkyl methyl benzyl ammonium chloride, CHG:

Chlorine; hypochlorite;

Chlorine dioxide; hydrogen peroxide; peracetic acid; glutaraldehyde;

N-4 dihydroxy-alpha-oxobenzene ethanimidoyl chloride;

1-alkyl(C16-18)amino-3-aminopropane acetate;

bis(trichloromethyl) sulfone;

5-chloro-2-methyl4-isothiazolin-3-one;

2-methyl4-isothiazolin-3-one;

2-(thiocyanomethylthio)-benzothiazole bis(trichloromethyl) sulfone.

Tris (hydroxymethyl) nitromethane (TN);

bromochlorodimethylhydantonin;

2-chloro4, 6-bis (ethylamino)-s-triazine;

phenolic with pentachlorophenate sodium salts of other chlorophenols

Potassium N. N-dimethyldithiocarbamate, 50%

Mixture of Disodium cyanothioimidocarbamate, N-methyldithiocarbamate, 20.3%

2.2-Dibromo-3-nitrilopropionamide, 20%

Hydroxyethyl2. 3-dibromopropionate, 30%

Poly (oxyethylene [dimethyliminiol] ethylene-(dimethyliminio) ethylene dichloride, 60%

Sodium pentachlorophenate

Calcium hypochlorite

Didecyidimethylammonium chloride

Hexahydro-1.3.-tris(2-hydroxyethyl)-s-triazine 4-(2-nitrobutyl) morpholine 4,4 (2-ethyl-2-nitrotrimethylene) dimorpholine Hexahydro-1.3.5.-tris(2-hydroxyethyl)-s-triazine Guanidines such as Dodecyl-guanidine HCl Bis(tri-N-butyl tin oxide)

o-phenylphenol and phenoxy ethanol o-benzyl-p-chlorophenol.

Other biocides such as those listed in "Disinfection, Sterilization, and preservation" by SE Block pp 385-389 (Lippincott, Williams & Wilkinson) may also be useful in performance of the invention.

However of those tested to date isothiazalin derivatives, nitroparaffins and combinations thereof are highly preferred.

The composition of the present invention preferably further includes a corrosion inhibitor, preferably an oxidising inhibitor or a film forming inhibitor.

According to a seventh aspect, the invention provides a shelf stable composition including an enzyme, a biocide and boron or a boron containing compound, said composition being compatible with film forming corrosion inhibitors.

According to an eighth aspect, the invention provides a concentrate including at least one enzyme, a corrosion inhibitor, a biocide and boron or a boron containing compound.

Examples of preferred formulations according to the present invention may include:

|  | Parts w/w |
|---|---|
| Water | 10-35 |
| Ethoxylated alcohol | 0-10 |
| Sodium Xylene sulfonate, 40% | 0-20 |
| m-pyrrolidone | 0-10 |
| Dipropylene glycol methyl ether (DPM) | 0-15 |
| CaCl2 5% soln. | 0.1-10 |
| Borax | 0-5 |
| 3,5-dichlorophenylboronic acid | 0-5 |
| Kathon WT | 1-15 |
| 2-bromo-2nitropropane-1,3 diol | 1-6 |
| Protease Alcalase 2.5 L | 5-25* |
| Amylase Thermamyl 300 DL | 1-25** |
| Cellulase Carezyme 1000 L | 1-20** |

*Of this the weight as dry protein is about 5.1%
**Of this the weight as dry protein is about 3.6%
***Of this the weight as dry protein is about 1%

Examples of alternative preferred formulations according to the present invention may include:

|  | Parts w/w |
|---|---|
| Water | 20-50 |
| CaCl2 5% | 1-10 |
| Boric acid | 1-10 |
| 3,5-dichlorophenylboronic acid | 1-3 |

-continued

|  | Parts w/w |
|---|---|
| Kathon WT | 1-15 |
| 2-bromo-2nitropropane-1,3 diol | 1-10 |
| Amylase | 1-15 |
| Cellulase | 5-25 |
| Lysozyme | 0.1-5 |
| Protease (Savinase 16 L) | 1-7 |

Additionally, it has been found that certain enzymes preferentially digest biofilm at different temperature ranges. Examples of enzymes which are better at the digestion of biofilm at low temperatures (cool or ambient temperature water) include:

Protease: Savinase, Chymotrypsin

Cellulase: 1,4(1,3;1,4)-beta-D-glucan 4-glocanohydrolase

Amylase: amylozyme, highdiastase

Lipase: L lipase, takamine lipase

Examples of enzymes which are found to digest biofilm at higher temperature, such as found in tepid or warmer water systems include:

Protease: Protinase T, Panazyme

Cellulase: Promalt, Oloclast

Amylase: Nervanase, Sbozzimante SPC

Lipase: Lipozyme,

BEST MODE FOR CARRYING OUT THE INVENTION

The invention will now be more particularly described by way of example only with reference to the accompanying data.

EXAMPLE 1

Effect of Various Corrosion Inhibitors and Various Biocides on Various Enzymes

Experiments conducted by the inventor have shown that enzymes are not stable in the presence of most corrosion inhibitors. Since abandoning chromium-based corrosion inhibitors and progressive phasing out molybdenum and inorganic phosphonates, fully organic corrosion inhibitors (such as 1-Hydroxyethylidene-1,1-diphosphonic acid, Sulfonate styrene/maleic anhydride copolymer, polyacrylates) have become industry standard. The latter group of inhibitors has detrimental effect on enzyme activity.

Experiments were conducted using the following:—

Corrosion Inhibitors and Concentrations:

|  | ppm |
|---|---|
| 1. Sodium molybdates | 10 and 100 |
| 2. phosphonates as hydroxy-phosphonoacetic acid | 100 and 1000 |

-continued

|  | ppm |
|---|---|
| 3. zinc salt as zinc chloride | 10 and 100 |
| 4. 1-Hydroxyethylidene-1,1-diphosphonic acid | 10 and 100 |
| 5. Polycarboxylate co-polymer (Acusol 445) | 10 and 100 |
| 6. Butynediolpolyethoxylate (Butyne 497) | 10 and 100 |

Biocides and Concentrations:

1.   5-chloro-2-methyl-4-isothiazolin-3-one+2-methyl-4-isothiazolin-3-one (Kathon WT)

2. 2,2-dibromo-3-nitrilopropionamide (Dowicide® 4)

3. Disodium ethylene bis-thiocarbamate (SC-2957)

4. Sodium dimethyl dithiocarbamate (Freshgard® 40)

5. Sodium Pentachloropeante (Dowicide® 7)

6. 2-bromo-2-nitropropane-1,3 diol (Myacide® AS)

All biocides were tested at 5, 15 and 100 ppm

| Enzymes and concentrations: | |
|---|---|
| Protease (Alcalase ® 2.5L) | 32 2.5 Au/g diluted 1000 times |
| Amylase (Takatherm ® 300 LX) | 300 kNu/g diluted 1000 times |

| pH: |
|---|
| pH of all samples was adjusted to 8 (common pH of cooling tower water). |

Enzyme Analysis

Throughout this specification (unless otherwise specified) the activity of proteases was assayed according to Novozymes standard test method No. B-863-GB (Manual Procedure for Determination Proteolytic Activity in Enzyme Preparations and Detergents (Azocasein substrate)).and the activity of amylases was assayed by Novozymes standard test method No. B 309d-GB (Manual Procedure for Determination Alpha-Amylase Activity in Enzyme Preparations and Detergents).

Procedure:

1. Add corrosion inhibitor or biocide to 100 mL of distilled water in a Schott bottle 2. Adjust pH to 8 with small quantities of NaOH and HCl 3. Place sample in a 30C water bath for 30 min 4 Add enzyme 5. Mix thoroughly and start stopwatch 6. Take 1 mL aliquots at 60 min, 2 hrs, 6 hrs, 24 hrs, 48 hrs and analyse enzyme activity 7. Report as percentage of the original activity.

The results are shown in tables 1-10

TABLE 1

Effect of corrosion inhibitors (low conc.) on protease
(Spiked with 2.5E-3 AU/g of protease)

| Corrosion inhibitor | Conc. ppm | 0 min % $A^o$ | 60 min % $A^o$ | 2 hrs % $A^o$ | 3 hrs % $A^o$ | 4 hrs % $A^o$ | 24 hrs % $A^o$ |
|---|---|---|---|---|---|---|---|
| Sodium molybdate | 10 | 100 | 13 | <2 | nt | nt | nt |
| 1-Hydroxy-ethylidene-1,1-diphosphonic acid | 100 | 100 | 29 | 7 | <2 | nt | nt |
| zinc chloride | 10 | 100 | <10 | <2 | <2 | nt | nt |
| benzotriazole | 10 | 100 | 14 | <2 | <2 | nt | nt |
| Polycarboxylate co-polymer (Acusol 445) | 10 | 100 | 21 | 8 | <2 | nt | nt |
| Butynediolpolyethoxylate (Butyne 497) | 10 | 100 | 26 | <2 | <2 | nt | nt |
| Control (dist water) | | 100 | 93 | 86 | 90 | 82 | 72 |

% $A^o$ in the tables is the percentage of the initial activity remaining at the time indicated.

TABLE 2

Effect of corrosion inhibitors (high conc.) on protease
(Spiked with 2.5E-3 AU/g of protease)

| Corrosion inhibitor | Conc. ppm | 60 min % $A^o$ | 2 hrs % $A^o$ | 3 hrs % $A^o$ | 4 hrs % $A^o$ | 24 hrs % $A^o$ |
|---|---|---|---|---|---|---|
| Sodium molybdate | 100 | <2 | <2 | nt | nt | nt |
| 1-Hydroxyethylidene-1,1-diphosphonic acid | 1000 | <2 | <2 | nt | nt | nt |
| zinc chloride | 100 | | <2 | nt | nt | nt |
| benzotriazole | 100 | | <2 | nt | nt | nt |
| Polycarboxylate co-polymer (Acusol 445) | 100 | <2 | <2 | nt | nt | nt |
| Butynediolpolyethoxylate (Butyne 497) | 100 | <2 | <2 | nt | nt | nt |
| Control (dist water) | | 93 | 86 | 90 | 82 | 72 |

TABLE 3

Effect of corrosion inhibitors (low conc.) on amylase
(Spiked with 300 Nu/p of amylase)

| Corrosion inhibitor | Conc. ppm | 60 min % $A^o$ | 2 hrs % $A^o$ | 3 hrs % $A^o$ | 4 hrs % $A^o$ | 24 hrs % $A^o$ |
|---|---|---|---|---|---|---|
| Sodium molybdate | 10 | 24 | 4 | <1 | nt | nt |
| 1-Hydroxyethylidene-1,1-diphosphonic acid | 100 | 22 | 5 | <1 | nt | nt |
| zinc chloride | 10 | 18 | 4 | <1 | nt | nt |
| benzotriazole | 10 | 31 | 4 | <1 | nt | nt |
| Polycarboxylate co-polymer (Acusol 445) | 10 | 33 | 6 | <1 | nt | nt |
| Butynediolpolyethoxylate (Butyne 497) | 10 | 19 | 4 | <1 | nt | nt |
| Control (dist water) | | 100 | 100 | 94 | 91 | 80 |

TABLE 4

Effect of corrosion inhibitors (high conc.) on amylase
(Spiked with 300 Nu/g of amylase)

| Corrosion inhibitor | Conc. after ppm | 60 min % $A^o$ | 2 hrs % $A^o$ | 3 hrs % $A^o$ | 4 hrs % $A^o$ | 24 hrs % $A^o$ |
|---|---|---|---|---|---|---|
| Sodium molybdate | 100 | 3 | <1 | nt | nt | nt |
| 1-Hydroxyethylidene-1,1-diphosphonic acid | 1000 ppm | 6 | <1 | nt | nt | nt |
| zinc chloride | 100 ppm | 4 | <1 | nt | nt | nt |
| benzotriazole | 100 ppm | 5 | <1 | nt | nt | nt |
| Polycarboxylate co-polymer (Acusol 445) | 100 ppm | 6 | <1 | nt | nt | nt |
| Butynediolpolyethoylate (Butyne 497) | 100 ppm | 6 | <1 | nt | nt | nt |
| Control (dist water) | | 100 | 100 | 94 | 91 | 80 |

TABLE 5

Effect of biocides (low conc.) on protease
(Spiked with 2.5E-3 AU/g of protease)

| | Conc. ppm | 60 min % $A^o$ | 2 hrs % $A^o$ | 3 hrs % $A^o$ | 4 hrs % $A^o$ | 24 hrs % $A^o$ |
|---|---|---|---|---|---|---|
| Kathon WT | 5 | 13 | <2 | nt | nt | nt |
| Dowicide 4 | 5 | 17 | <2 | nt | nt | nt |
| SC-2957 | 5 | 12 | <2 | nt | nt | nt |
| Freshgard 40 | 5 | 19 | <2 | nt | nt | nt |
| Dowicide 7 | 5 | 23 | <2 | nt | nt | nt |
| Myacide AS | 5 | 9 | <2 | nt | nt | nt |
| Control (dist water) | | 93 | 86 | 90 | 82 | 72 |

TABLE 6

Effect of biocides (high conc.) on protease
(Spiked with 2.5E-3 AU/g of protease)

| | Conc. ppm | 60 min % $A^o$ | 2 hrs % $A^o$ | 3 hrs % $A^o$ | 4 hrs % $A^o$ | 24 hrs % $A^o$ |
|---|---|---|---|---|---|---|
| Kathon WT | 15 | 10 | <2 | nt | nt | nt |
| Dowicide 4 | 15 | 11 | <2 | nt | nt | nt |
| SC-2957 | 15 | 7 | <2 | nt | nt | nt |
| Freshgard 40 | 15 | 4 | <2 | nt | nt | nt |
| Dowicide 7 | 15 | 9 | <2 | nt | nt | nt |
| Myacide AS | 15 | 11 | <2 | nt | nt | nt |
| Control (dist water) | | 93 | 86 | 90 | 82 | 72 |

TABLE 7

Effect of biocides on protease
Spiked with 2.5E-3 AU/g of protease

|  | Conc. ppm | 60 min % $A^0$ | 2 hrs % $A^0$ | 3 hrs % $A^0$ | 4 hrs % $A^0$ | 24 hrs % $A^0$ |
|---|---|---|---|---|---|---|
| Kathon WT | 100 | 7 | <2 | nt | nt | nt |
| Dowicide 4 | 100 | 11 | <2 | nt | nt | nt |
| SC-2957 | 100 | <2 | <2 | nt | nt | nt |
| Freshgard 40 | 100 | 7 | <2 | nt | nt | nt |
| Dowicide 7 | 100 | <2 | <2 | nt | nt | nt |
| Myacide AS | 100 | <2 | <2 | nt | nt | nt |
| Control (dist water) |  | 93 | 86 | 90 | 82 | 72 |

TABLE 8

Effect of biocides on amylase
(Spiked with 300 Nu/g of amylase)

|  | Conc. ppm | 60 min % $A^0$ | 2 hrs % $A^0$ | 3 hrs % $A^0$ | 4 hrs % $A^0$ | 24 hrs % $A^0$ |
|---|---|---|---|---|---|---|
| Kathon WT | 5 | 34 | 4 | <1 | nt | nt |
| Dowicide 4 | 5 | 19 | <1 | <1 | nt | nt |
| SC-2957 | 5 | 29 | 5 | <1 | nt | nt |
| Freshgard 40 | 5 | 37 | <1 | <1 | nt | nt |
| Dowicide 7 | 5 | 40 | 5 | <1 | nt | nt |
| Myacide AS | 5 | 32 | 6 | <1 | nt | nt |
| Control (dist water) |  | 100 | 100 | 89 | 91 | 86 |

TABLE 9

Effect of biocides on amylase
(Spiked with 300 Nu/g of amylase)

|  | Conc. ppm | 60 min % $A^0$ | 2 hrs % $A^0$ | 3 hrs % $A^0$ | 4 hrs % $A^0$ | 24 hrs % $A^0$ |
|---|---|---|---|---|---|---|
| Kathon WT | 15 | 35 | <1 | nt | nt | nt |
| Dowicide 4 | 15 | 13 | <1 | nt | nt | nt |
| SC-2957 | 15 | 13 | <1 | nt | nt | nt |
| Freshgard 40 | 15 | 22 | <1 | nt | nt | nt |
| Dowicide 7 | 15 | 31 | 3 | <1 | nt | nt |
| Myacide AS | 15 | 37 | 9 | <1 | nt | nt |
| Control (dist water) |  | 100 | 100 | 89 | 91 | 86 |

TABLE 10

Effect of biocides on amylase
(Spiked with 300 Nu/g of amylase)

|  | Conc. ppm | 60 min % $A^0$ | 2 hrs % $A^0$ | 3 hrs % $A^0$ | 4 hrs % $A^0$ | 24 hrs % $A^0$ |
|---|---|---|---|---|---|---|
| Kathon WT | 100 | <1 | nt | nt | nt | nt |
| Dowicide 4 | 100 | 10 | <1 | nt | nt | nt |
| SC-2957 | 100 | <1 | <1 | nt | nt | nt |
| Freshgard 40 | 100 | 7 | <1 | nt | nt | nt |
| Dowicide 7 | 100 | <1 | <2 | nt | nt | nt |
| Myacide AS | 100 | <1 | <2 | nt | nt | nt |
| Control (dist water) |  | 100 | 100 | 89 | 91 | 86 |

Notes:
In Tables 1-10:
% $A^0$ is the percentage of the initial activity remaining at the time indicated.
Amylase activity analysis has detection limit of 0.03 Nu/g (1% of the spiked activity of 3 Nu/g);
Protease activity analysis has detection limit of 5*E-7 Au/g (2% of the spiked activity of 2.5E-5 Au/g)
nt = "not tested" (when activity of the previous time point was below the detection limit).

EXAMPLE 2

Effectiveness of Formulations According to the Invention

The examples below show the effectiveness of formulations according to the invention and the data shown in Tables 11 to 13 exemplify the invention.

| Corrosion inhibitors tested and concentrations: | |
|---|---|
| 1. Sodium molybdate | 100 ppm, |
| 2. phosphonates as hydroxy-phosphonoacetic acid | 1,000 ppm, |
| 3. zinc salt as zinc chloride | 100 ppm |
| 4. 1-Hydroxyethylidene-1,1-diphosphonic acid | 100 ppm |
| 5. Polycarboxylate co-polymer (Acusol 445) | 100 ppm |

| Enzymes tested and concentrations | |
|---|---|
| Amylase (Termamyl 300) | 300 Knu/g diluted 1000 times |

| pH: |
|---|
| pH of all samples was adjusted to 8 (common pH of cooling tower water). |

Procedure:

1. Add corrosion inhibitor to 100 mL of distilled water in Schott bottle

2. Adjust pH to 8 with small quantities of NaOH

3. Adjust temperature to 30C in water bath for 30 min

4. Add 15 ppm of isothiazolin (Kathon WT) and 15 ppm of 2-bromo-2nitropropane-1,3 diol 5. Add enzyme 6. Mix thoroughly and start stopwatch.

7. Take 1 mL aliquots at 15 min, 60 min, 24 hrs, 48 hrs and analyse enzyme activity 8. Report as percentage of the original activity.

| Formulations according to the invention tested: | |
|---|---|
| 1. Termamyl 300 L | 20* |
| Propylene Glycol | 16 |
| Borax | 2 |
| Glycerol | 4 |
| Teric 164 | 1 |
| dry weight as protein about 3.6% of weight of enzyme) | |
| 2. Termamyl 300 L | 20 |
| Propylene Glycol | 16 |
| Borax | 4 |
| Glycerol | 4 |
| Teric 164 | 1 |
| 3. Termamyl 300 L | 20 |
| Propylene Glycol | 16 |
| Borax | 6 |
| Glycerol | 6 |
| Sodium formate | 1 |

The results are set out in tables 11-13

TABLE 11

Effect of corrosion inhibitors on amylase with boron.
Formulation 1 (low borax) -Spiked with 300 Nu/g of amylase

| Corrosion inhibitor | % A° 15 min | % A° 60 min | % A° 24 hrs | % A° 48 hrs |
|---|---|---|---|---|
| Sodium molybdate | 79.19 | 83.84 | 46.64 | 39.2 |
| 4.1-Hydroxyethylidene-1,1-diphosphonic acid | 78.26 | 64.31 | 67.1 | 42.92 |
| zinc chloride | 85.7 | 88.49 | 61.52 | 57.8 |
| benzotriazole | 95 | 95 | 39.2 | 43.85 |
| Polycarboxylate co-polymer (Acusol 445) | 85.7 | 74.54 | 42.92 | 30.83 |
| Control (dist water) | 100 | 100 | 73 | 44 |

TABLE 12

Effect of corrosion inhibitors on amylase with boron.
Formulation 2 (high borax) -Spiked with 300 Nu/g of amylase

| | % A° 15 min | % A° 60 min | % A° 24 hrs | % A° 48 hrs |
|---|---|---|---|---|
| Sodium molybdate | 90.3 | 95.7 | 52.2 | 43.5 |
| 4.1-Hydroxyethylidene-1,1-diphosphonic acid | 89.2 | 72.8 | 76.1 | 47.8 |
| zinc chloride | 96.0 | 98.0 | 69.6 | 65.2 |
| benzotriazole | 100.0 | 97.0 | 43.5 | 48.9 |
| Polycarboxylate co-polymer (Acusol 445) | 89.0 | 84.8 | 47.8 | 33.7 |
| Control (dist water) | 100 | 100 | 73 | 44 |

TABLE 13

Effect of corrosion inhibitors on amylase with boron.
Formulation 3 (high borax + formate) -Spiked with 300 Nu/g of amylase

| Spiked with 300 nU/g | % A° 15 min | % A° 60 min | % A° 24 hrs | % A° 48 hrs |
|---|---|---|---|---|
| Sodium molybdate | 90.3 | 90.0 | 71.0 | 49.8 |
| 4.1-Hydroxyethylidene-1,1-diphosphonic acid | 89.2 | 72.8 | 70.0 | 54.7 |
| zinc chloride | 96.0 | 90.0 | 93.6 | 74.2 |
| benzotriazole | 100.0 | 100.0 | 59.6 | 55.9 |
| Polycarboxylate co-polymer (Acusol 445) | 89.0 | 91.0 | 65.3 | 38.9 |
| Control (dist water) | 100 | 100 | 73 | 44 |

EXAMPLE 3

Comparison Between Preferred Embodiments and Prior Art

Method:

The following non-oxidising biocides are currently used in cooling towers:

1. 5 chloro-2 methyl 4 isothiazolin-3-one+2 methyl 4 isothiazblin-3-one (Kathon WT, Calgon H510, etc)

2. 2,2-dibromo-3-nitrilopropionamide (Dowicide® 4)

3. Disodium ethylene bis-thiocarbamate (SC-2957 from Calgon®)

4. Sodium dimethyl dithiocarbamate (Freshgard® 40, alcobam® nm; brogdex® 555; carbon s)

5. Sodium pentachloropeante (Dowicide® 7)

6. 2-bromo-2nitropropane-1,3 diol (Myacide® AS)

All biocides were tested at 100 ppm active

Enzymes Tested and Concentrations

| Enzymes tested and concentrations | |
|---|---|
| Amylase (Alcalase ® 2.5DXL) | 2.5 Au/g diluted 1000 times | pH:

pH of all samples was adjusted to 8 (common pH of cooling tower water).

Procedure:

1. Add biocide to 100 mL of distilled water in Schott bottle

2. Adjust pH to 8 with small quantities of NaOH

3. Bring to 30C in water bath (keep for approx. 30 min)

4. Add enzyme

5. Mix thoroughly and start stopwatch

6. Take 1 mL aliquots at 30 min, 2 hrs, 24 hrs, 48 hrs and analyse enzyme activity 7. Report as percentage of the original activity.

| Formulations tested: | |
|---|---|
| 4. Termamyl 300 DX | 20 |
| Propylene Glycol | 16 |
| Borax | 4 |
| Glycerol | 4 |
| Teric 164 | 1 |
| 5. Termamyl 300 DX | 20 |
| Propylene Glycol | 16 |
| Borax | 6 |
| Glycerol | 6 |
| Sodium formate | 1 |

The results are set out in tables 14 -15

TABLE 14

Amylase (formulation 4 with borax only) and biocides

| Biocide | Result |
|---|---|
| isothiazolin(Kathon WT) | Fair to good stability with 40% remaining after 48 hrs |
| nitrilopropionamide (Dowicide 4) | No activity remains after 4 hrs |
| Sodium dimethyl dithiocarbamate (Freshgard 40) | No activity remains after 4 hrs |
| Sodium Pentachloropeante (Dowicide 7) | No activity remains after 2 hrs |
| 2-bromo-2nitropropane-1,3-diol (Myacide AS) | Good to excellent stability with ~67% remaining after 24 hrs and >45% after 48 hrs |
| Control (deionised water) | ~70% after 24 hrs and ~55% after 48 hrs |

TABLE 15

Protease (formulation 5 with borax + formate) and biocides

| biocide | result |
|---|---|
| isothiazolin(Kathon WT) | good stability with ~48% remaining after 48 hrs |
| nitrilopropionamide (Dowicide 4) | No activity remains after 2 hrs |
| Sodium dimethyl dithiocarbamate (Freshgard 40) | No activity remains after 2 hrs |
| Sodium Pentachloropeante (Dowicide 7) | No activity remains after 2 hrs |
| 2-bromo-2nitropropane-1,3 diol (Myacide AS) | Good to excellent stability with ~65% remaining after 24 hrs and ~40% after 48 hrs |
| Control (deionised water) | ~70% after 24 hrs and ~55% after 48 hrs |

EXAMPLE 4

Effect of Corrosion Inhibitors on Prior Art

A synthetic cooling tower water with biocide and corrosion inhibitor is spiked with known level of enzymes. After exposure of enzymes to the denaturing action of corrosion inhibitors and/or biocides for a pre-determined period of time (1,2,6,24 hrs), a known amount of a bacterial/fungal inoculum is added to the cooling water. This is to simulate a typical situation in cooling towers when microorganisms are introduced as a result of disturbing biofilm.

The microorganisms are exposed to the combination of an enzymes with cooling water containing corrosion inhibitors for 1 hr.

After 60 minutes the survivors are quantified using standard plate count technique.

Media

Tryptone Water

Saline water in 25 ml bottles (sterile).

Test Organism

*P.aeruginosa* ATCC 15442

*Aerobacter levanicum* ATCC 15552

*Rhodotorula glutinis* ATCC 2527

*Bacillus subtilis* ATCC 19659

Preparation

Transfer a loopful of organism into 3×10 ml Tryptone Soya broth. Grow overnight at 36° C. Divide culture into 10×3 ml aliquots in 25 ml sterile universal bottles.

Enzymes

Protease—Alkalase 2.5 DX ex Novozymes

Amylase—Termamyl 300 DX ex Novozymes

Levanbiohydrolase from Rhodotorula glutinis cell culture filtered through 0.2 micron filter concentrate equivalent 730 units/mL Biocides Methylene-bis-thiocyanate (MBT) ex Merck Dimethyl Dithiocarbamate (13%)+Disodium Ethylbis-dithiocarbamate (15%) (Carbamate) ex Prentiss Control Sterile distilled water Test Procedure 1. Prepare simulated cooling tower water by adding 40 ppm of zinc phosphonate corrosion inhibitor (Designated "ci" in tables)

2. Add 200 ppm of chloride ions as sodium chloride and 200 ppm of sulfate ions as sodium sulfate in 6×100 mL sterile jars. Add biocide at pre-defined level 3. Add enzymes in pure or formulated form to achieve end concentrations of 2.5E-3 Au/g of 300 Nu/g for protease and amylase respectively 4. Place jars in water bath at 30C. Start stopwatch 5. At time T=1 hr add inoculum to first jar to achieve bacterial population of ~10E+6 cfu/mL 6. Digest bacterial inoculum for 45 min 7. Quantify the surviving bacteria by plating using serial dilutions 8. Report result for 1 hr exposure of enzymes to cooling water 9. Repeat steps 5-8 for exposure times of 2, 4, 6 and 24 hours.

Note: in order to differentiate between treatment regimen the biocide is used at concentrations that allows achievement of 2-3 log reduction in bacterial population during 45-min treatment.

Results:

The results are summarized in table 16

TABLE 16

Biocidal efficacy of synergistic enzyme-biocide combination. Cfu log reduction in cooling tower water using unformulated enzymes. Water is spiked with *Aerobacter levanicum* bacteria 2.3E+6 cfu/ml

| exp | Biocide | biocide, ppm | Log red'n after 1 hr | Log red'n after 2 hr | Log red'n after 4 hrs | Log red'n after 6 hrs | Log red'n after 24 hrs |
|---|---|---|---|---|---|---|---|
| 1 | MBT + no enzyme + ci | 22 | >5 | 3.1 | nt | nt | 2.7 |
| 2 | MBT + levan biohydrolase, no ci | 22 | >5 | >5 | nt | 4.0 | 2.9 |
| 3 | MBT + protease and amylase + ci | 22 | 4.2 | 3.0 | 1.7 | <2 | <2 |
| 4 | MBT + levan biohydrolase + ci | 22 | 3.3 | <1 | <1 | <1 | <1 |
| 5 | Carbamate + protease and amylase + ci | 25 | 4.7 | <1 | <1 | <1 | <1 |

EXAMPLE 5

Examples According to Invention for Comparison with Prior Art (Example 4)

In this example the method and materials were as described for example 4. However the following enzyme formulations according to the invention were substituted:

| 6. Alcalase 2.5DXL | 20 |
| --- | --- |
| Thermamyl 300DX | 20 |
| Propylene Glycol | 16 |
| Borax | 4.5 |
| Glycerol | 4 |
| 7. Alcalase 2.5DXL | 20 |
| Thermamyl 300DX | 20 |
| Propylene Glycol | 16 |
| 3,5-dichlorophenylboronic acid | 2 |
| Glycerol | 4 |
| Teric 164 | 1 |

The results are shown in table 17-20 with four different micro-organisms:

TABLE 17

Biocidal efficacy of synergistic enzyme-biocide combination.
Cooling tower water and formulated enzymes
Spiked with *Aerobacter levanicum* bacteria 2.3E+6 cfu/ml

| Exp. | Biocide | Conc. of biocide ppm | Log red'n after 1 hr | Log red'n after 2 hr | Log red'n after 4 hrs | Log red'n after 6 hrs | Log red'n after 24 hrs |
| --- | --- | --- | --- | --- | --- | --- | --- |
| 1 | Formulation 7 + Kathon WT + ci | 8 | >5 | >5 | nt | >5 | >5 |
| 2 | MBT, no enzyme | 22 | 3.3 | nt | nt | nt | 3.0 |
| 3 | MBT + (formulation 2) + ci | 22 | 4.4 | >5 | nt | 4.4 | 4.6 |
| 4 | MBT + levan biohydrolase + 0.1% borax + ci | 22 | 4.0 | 3.1 | 2.3 | 2.5 | 2.0 |
| 5 | Carbamate + (formulation 7) + ci | 25 | 4.7 | 4.1 | 3.8 | 4.5 | 3.9 |

TABLE 18

Biocidal efficacy of synergistic enzyme-biocide combination.
Cooling tower water and formulated enzymes
Spiked with *P. aerugnosa* bacteria 1.9E+7 cfu/ml

| Biocide | Conc. of biocide ppm | Log red'n after 1 hr | Log red'n after 2 hr | Log red'n after 4 hrs | Log red'n after 6 hrs | Log red'n 24 hrs |
| --- | --- | --- | --- | --- | --- | --- |
| Kathon WT + protease and amylase - no boron | 12 | 3.6 | 2.4 | 2.6 | 2.6 | 2.8 |
| Kathon WT + protease and amylase (formulation 7) | 12 | >5 | >5 | >5 | >5 | >5 |
| MBT, no enzyme (CONTROL 1) | 55 | 3.3 | nt | nt | nt | 3.0 |
| MBT + protease and amylase(formulation 2) | 55 | >5 | >5 | >5 | 4.6 | >5 |
| MBT + levan biohydrolase + 0.1% borax | 55 | 3.5 | 3.1 | 2.3 | 2.5 | 2.0 |
| Carbamate + protease and amylase (formulation 7) | 95 | >5 | >5 | >5 | >5 | >5 |
| Carbamate without enzymes (control 2) | 95 | 3.2 | Nt | Nt | Nt | 3.4 |

TABLE 19

Biocidal efficacy of synergistic enzyme-biocide combination.
Cooling tower water and formulated enzymes
Spiked with *Rhodotorula glutinis* yeast 8.7E+5 cfu/ml

| Biocide | Conc. Of biocide ppm | Log red'n after 1 hr | Log red'n after 2 hr | Log red'n after 4 hrs | Log red'n after 6 hrs | Log red'n after 24 hrs |
| --- | --- | --- | --- | --- | --- | --- |
| Kathon WT + protease and amylase no boron | 10 | 2.7 | 2.4 | nt | nt | 2.8 |
| Kathon WT + protease and amylase (formulation 7) | 10 | >5 | >5 | >5 | >5 | >5 |
| MBT, no enzyme (CONTROL 1) | 15 | 3.0 | nt | nt | nt | 2.6 |
| MBT + protease and amylase (formulation 2) | 15 | >5 | >5 | >5 | >5 | >5 |
| MBT + levan biohydrolase + 0.1% borax | 15 | 2.9 | nt | 2.9 | Nt | 3.1 |
| Carbamate + protease and amylase (formulation 7) | 35 | >5 | >5 | >5 | >5 | >5 |
| Carbamate without enzymes (control 2) | 35 | 2.6 | Nt | Nt | Nt | 2.9 |

*Bacillus subtilis* ATCC 19659

TABLE 20

Biocidal efficacy of synergistic enzyme-biocide combination.
Cooling tower water.
Spiked with *Bacillus subtilis* ATCC 19659 bacteria 4.3E+6 cfu/ml

| Biocide | Conc. Of biocide ppm | Log red'n after 1 hr | Log red'n after 2 hr | Log red'n after 4 hrs | Log red'n after 6 hrs | Log red'n after 24 hrs |
| --- | --- | --- | --- | --- | --- | --- |
| Kathon WT + protease and amylase no boron | 10 | 3.0 | 2.1 | nt | nt | 2.9 |
| Kathon WT + protease and amylase (formulation 7) | 10 | >5 | >5 | >5 | >5 | >5 |
| MBT, no enzyme (CONTROL 1) | 25 | 2.7 | nt | nt | nt | 2.9 |
| MBT + protease and amylase (formulation 2) | 25 | >5 | >5 | >5 | >5 | >5 |
| Carbamate + protease and amylase (formulation 7) | 35 | >5 | >5 | >5 | >5 | >5 |
| Carbamate without enzymes (control 7) | 35 | 3.8 | Nt | Nt | Nt | 3.4 |

EXAMPLE 6

The biocidal efficacy against *Legionella* of water treatment agents according to the invention were compared with enzyme/biocide combinations not according to the invention in corrosion inhibited water. Handling *Legionella* requires special precautions and the test method developed is set out in appendix 1. Two formulations were tested.

Formula 6 (No boron Comparison)

| | |
|---|---|
| Alcalase 2.5DXL | 20 |
| Thermamyl 300DX | 20 |

Formula 7 (Containing Borax in Accordance with the Invention):

| | |
|---|---|
| Alcalase 2.5DXL | 20 |
| Thermamyl 300DX | 20 |
| Propylene Glycol | 16 |
| Borax | 4.5 |
| Glycerol | 4 |
| Water | QC |

The results are shown in Table 21

TABLE 21

Effect of formula according to the invention on *Legionella*

| Treatment | Digestion Time(hrs) | Before biocide Log Treatment | After biocide Log Treatment | Log Reduction |
|---|---|---|---|---|
| Formula 7 | 1 | 2.55 xE4 | 4.5 xE2 | 1.75 |
| Formula 7 | 4 | 4.65 xE4 | <10 | >4 |
| Formula 7 | 6 | 3.32 xE4 | <10 | >4 |
| Formula 7 | 24 | 3.9 xE4 | <10 | >4 |
| Formula 6 | 1 | 2.85 xE4 | 50 | 2.75 |
| Formula 6 | 4 | 4.85 xE4 | 2.55 xE2 | 2.27 |
| Formula 6 | 6 | 3.75 xE4 | 2.55 xE3 | 1.16 |
| Formula 6 | 24 | 3.95 xE4 | 6.45 xE3 | 0.787 |

EXAMPLE 7

The following formulations represent preferred embodiments adapted for use in particular situations and are illustrative examples of the way in which the invention is applied in practice. The formulations are concentrates which diluted in use as indicated or as otherwise appropriate.

Formulation 8

Formulation 8 is a cleaning solution for initial (periodic, e.g. quarterly) cleaning of cooling towers. To be added at rate 100-1000 mL per 1 tonne of cooling water depending on the condition of cooling tower:

| | Parts w/w |
|---|---|
| Water | 11.9 |
| Ethoxylated alcohol | 7 |
| Sodium Xylene sulfonate, 40% | 15 |
| m-pyrrolidone | 7.3 |
| CaCl2 5% soln. | 6 |
| Borax | 3 |
| Kathon WT | 8.2 |
| 2-bromo-2nitropropane-1,3 diol | 4.6 |
| Protease Alcalase 2.5 L | 17 |
| Amylase Thermamyl 300 DL | 23 |
| Cellulase Carezyme 1000 L | 4 |

To be re-circulated for 48-72 hours (usually over-the-weekend).

Formulation 9

Formulation 9 is similar to formulation 8 but for use with high biofilm content systems:

| | Parts w/w |
|---|---|
| water | 29.9 |
| Ethoxylated alcohol | 7 |
| Sodium Xylene sulfonate, 40% | 15 |
| Dipropylene glycol methyl ether (DPM) | 12 |
| CaCl2 5% soln | 1 |
| 3,5-dichlorophenylboronic acid | 1.5 |
| Kathon WT | 11 |
| 2-bromo-2nitropropane-1,3 diol | 2 |
| Protease Alcalase 2.5 L | 11 |
| Amylase Thermamyl 300 DL | 2 |
| Cellulase Carezyme 1000 L | 14.6 |

Formulation 10

Formulation 10 is a maintenance solution for on-going addition to cooling water (at least once every 48 hours) to maintain concentration of 2-bromo-2nitropropane-1,3 diol of 7-15 ppm in the cooling water

| | Parts w/w |
|---|---|
| Water | 34.6 |
| CaCl2 5% | 8 |
| Boric acid | 6.1 |
| Kathon WT | 13 |
| 2-bromo-2nitropropane-1,3 diol | 6.5 |
| Amylase | 11.3 |
| Cellulase | 19 |
| Lysozyme | 1.5 |

Formulation 11

Same as 10 but for older cooling towers (e.g. such as open to atmosphere, high organic load, made out of wood etc.)

| | Parts w/w |
|---|---|
| Water | 40.1 |
| CaCl2 5% | 8 |
| Boric acid | 3.5 |
| 3,5-dichlorophenylboronic acid | 0.6 |
| Kathon WT | 13 |
| 2-bromo-2nitropropane-1,3 diol | 6.5 |
| Amylase | 11.3 |
| Cellulase | 12 |
| Protease (Savinase 16 L) | 5 |

DISCUSSION OF RESULTS

Example 1, Tables 1-4, show that enzymes such as protease and amylase at both low and high concentrations are reduced to less than about 2% of their original activity (i.e. to below the threshold of detection in these experiments) in the presence of a wide range of corrosion inhibitors within about 2 hours in most cases, and are substantially ineffective within one hour in most cases at affordable concentrations. in no case was the concentration above 2% of the starting concentration after 3 hours.

Example 1, Tables 5-10, show that biocides similarly reduce the efficacy of the enzymes to less than 1 or 2% of their starting concentration within about 2 to 3 hours after addition at both low and high concentrations.

Example 2, tables 11 to 13, demonstrate that pre-conditioning of enzymes with boron compounds according to the invention serves to maintain their activity in the presence of commercially useful concentrations of common corrosion inhibitors. in each case the enzyme maintains at least about 40% and in some cases above 60% of its activity for 24 hours in the case of preferred embodiment formulation 3 the activity retained is from about 60% to about 90% after 24 hours.

Preferably the boron compound is combined with a solvent and more particularly with a solvent which facilitates dissolution of the boron in water for example a polyol such as propylene glycol. in the examples shown in tables 11 to 13, the biocides were introduced into the "cooling water" in concentrations such as are in general use. The compositions of the invention extend the enzyme activity in a bulk water environment sufficiently to make simultaneous addition of a isothiazolin and/or nitroparaffin biocide with enzyme a commercially feasible alternative to the use of biocides alone, but at much reduced biocide concentration in comparison to the prior art use of biocide alone. Example 3, tables 14 and 15, shows that of several common biocides trialed, formulations according to the invention in which an isothiazolin biocide (Kathon® KT-5 chloro-2 methyl 4 isothiazolin-3-one+2 methyl 4 isothiazolin-3-one) and a nitroparaffin biocide (2-bromo-2nitropropane-1,3) were selected as the biocide for use unexpectedly gave surprisingly superior results in combination with enzymes. The preferred combination maintained activity over a long period even in the presence of corrosion inhibitors, and even when the concentration of the biocides exceed recommended concentrations in cooling tower by a factor of 10-15.

Example 4 (table 16—exp 1) shows that the Pederson prior art preferred biocide, MBT, at 22 ppm in the absence of an enzyme gives at least a 5 log reduction after 1 hr and remains better than 50% effective after 24 hrs. Moreover in the presence of the preferred enzyme, but absence of a corrosion inhibitor (exp. 2), MBT gives the same or better results as in the absence of the enzyme over 2 hrs but not over 24 hrs. However, in the presence of a corrosion inhibitor, the MBT plus Levan Biohydrolase prior art combination fails (exp. 4). The presence of corrosion inhibitor reduces the effectiveness of the MBT/levan biohydrolase combination to less than the that of the MBT alone within 1 hour (exp 4), and the combination has an effectiveness of less than 1 log reduction after less than 2 hours. This means that in practice the continuous addition of enzyme or repeated addition at intervals of about one hour would be required which would create serious enzyme activity monitoring problems, and make the process totally uneconomical for use in bulk water or air conditioning systems. These results are consistent with Pederson's own data. Pederson's experiments (in a system which did not contain corrosion inhibitors) showed that when the biocide was added 2 hours after enzyme addition the improvement of the combination over the biocide alone was less than 1 log although Pederson did not comment on this. Example 5 (table 17) shows that formulations according to the present invention are significantly more effective than the prior art combination in the presence of a corrosion inhibitor (as exemplified by Table 16 exp 3). Table 17 exp 1 shows that preferred embodiments formulated according to the invention, retain their effectiveness after 24 hours even in the presence of denaturing corrosion inhibitors and/or biocides. The biocidal action of the combination is significantly better than biocide alone. Even the MBT/Levan biohydrolase combination from the prior art when conditioned with a boron compound according to the invention (table 17—exp.4) retains some activity for 24 hours. However, under conditions found in cooling towers, the MBT/Levan biohydrolase is among the least effective of the tested combinations according to the invention.

Table 18 shows that the results obtained with Aerobacter levanicum (table 17) are equally applicable in the case of *P. aerugnosa* bacteria(table 18). Combinations according to the invention in which the enzymes are combined with boron or boron compounds have increased stability against the denaturing action of corrosion inhibitors and/or biocides. The biocidal action of the combined boron plus enzyme plus biocide is significantly better than biocide alone, whilst non-formulated enzymes after 1 hour show little or no improvement in biocidal action over biocide alone. Note a significant increase in concentrations of all biocides because *P. aeruginosa* is more resistant to the biocides.

Table 19, 20 shows that similar results are evident with *Rhodoturula glutinis* yeast, and *B. subtilis* respectively. Again the enzymes plus boron are more stable against the denaturing action of corrosion inhibitors and/or biocides. The fungicidal action of the combined [boron plus enzyme plus biocide] is significantly better than biocide alone.

Table 21 shows that in water treated with corrosion inhibitors and containing *Legionella*, treatments according to the invention result in a 4 log reduction in *Legionella* after 4 hours and for up to at least 24 hours. in contrast, a simple combination of the same enzymes and biocide in the presence of corrosion inhibitors but in the absence of preconditioning with a boron compound does not maintain its activity beyond about 2 hours, giving an almost undetectable log reduction in *Legionella* after 6 hours.

EXAMPLE 8

Tepid Water System Remediation Trial.

A tepid water system remediation trial was conducted in a hospital under the scrutiny of appropriate Health Department officers. The institution was a tepid water system whose temperature range was 46.5 to 49.1° C. The treatment took place overnight with all access to the tepid water outlets being barred for the six hours of the trial. The product used was a two part product, the first part containing the conditioned enzyme, the second the biocide. Both parts were added into the bulk water system at a rate of 200 to 250 parts of water to 1 part product. The product was dosed into the circuit via a tepid water storage tank. All the taps and showers were opened slightly to ensure some small flow, with the water running to waste.

The enzymes which have been found to be particularly suited to digest biofilm at higher temperature in accordance with the present invention, such as found in tepid or warmer water systems include the following Proteases such as Protinase T, Panazyme; Cellulases such as Promalt, Oloclast; Amylases such as Nervanase, Sbozzimante SPC; and Lipases such as Lipozyme, Any or all of these are suited for remediation of tepid water systems.

Water samples were taken from various sampling points on the tepid water circuit for microbiological assessment prior to the trial. After six hours, all the taps and showers were fully opened so as to dissipate the product dosed in the system. A food grade dye was added as an indicator, and the absence of a visible detectable colour indicated a safe level (parts per million) of the enzyme. The water was sampled after completion of the water rinse cycle. The tepid water system was then put into normal service, and sampled again after six days. The collection technique involved collecting a sample for 30 seconds. All the water temperatures were in the 46.5 to 49.1° C. ranges disclosed above.

| Sampling point | Description of water outlet | *Legionella pneumophilia* count ufc/liter | | |
|---|---|---|---|---|
| | | prior to treatment | post treatment | six days post treatment |
| Exit Tank 1 | High Flow Rate tap | 800 | 50 | <50 |
| Return Circle | High Flow Rate tap | 1100 | 300 | <50 |
| Reception | Wash sink tap | 350 | — | <50 |
| Ward 101 | Wash sink tap | 100 | — | <50 |
| Ward 201 | Wash sink tap | 100 | 50 | <50 |
| Ward 301 | Wash sink tap | 100 | <50 | <50 |

The results showed a significant level of remediation of the tepid water system. On the basis of the above results, the remediation would be repeated monthly.

For use in lower temperature systems, such as cool or ambient temperature water, the following enzymes have been found to be more particularly suited: Proteases such as Savinase, Chymotrypsin; Cellulases such as 1,4(1,3;1,4)-beta-D-glucan 4-glocanohydrolase; Amylases such as amylozyme, highdiastase and Lipases such as L lipase, takamine lipase.

The two can be used in conjunction, using the higher temperature enzyme systems to clean the hot water system, and the low temperature enzyme systems to treat the cold water systems. Alternatively, both can be employed on the same system to planktonise sessile biofilm if the temperature profile of the whole water system warrants this or is unknown.

Thus, in summary, corrosion is a major problem in recirculating water systems. The existence of micro-organisms is also a major problem in those systems. Enzymes are deactivated by modem acceptable corrosion inhibitors and by biocides. Biocides alone, at safe levels of use, are not effective in killing both sessile and planktonic bacteria. Combinations of biocide and enzyme which have been suggested in the past are not effective in systems containing corrosion inhibitors because the enzymes are substantially deactivated in less than an hour, and because at safe levels of use biocides require much longer than that to be effective. The vast majority of non-oxidising biocides kill bacteria via absorption onto the cell membrane. Biocides can also absorb onto enzyme proteins thus biocides also effectively deactivate enzymatic activity. Similar problems occur in tepid water systems wherein sessile micro-organisms are harboured within a biofilm. Hitherto it has been usual to treat such systems with chlorine agents such as hypochlorite, but these have only been effective against planktonic micro-organisms, leaving sessile micro-organisms viable within the biofilm.

The present inventor has found that by adding or increasing the concentration of boron in the formulation sufficiently, a point can be reached at which the enzyme will retain at least 40% of its activity for 24 hours, and in some cases can retain almost 100% of its activity for that period. Those skilled in the art will appreciate that compositions according to the invention may use combinations of enzymes and biocides other than those exemplified and may formulate the compositions in other concentrations and with other additives without departing from the inventive concept herein disclosed.

Appendix 1

Method for Testing the Effect of Enzyme/Biocide Combinations on Cooling Water Containing *Legionella*.

Method developed to determine the bactericidal efficacy of cooling tower disinfectants against *Legionella pneumophilia* organism present in biofilm form isolated and treated with different enzyme formulations.

Unusual Safety Precautions

The following experiment involves *Legionella pneumophilia* which is potentially pathogenic bacteria. This test method involves bacterial cell counts exceeding well above the minimum infective dose.

The test should be carried out in Class 2 Laminar flow cabinet

Principle

The *Legionella* bacteria can be found in three forms, free floating planktonic form, grown as a biofilm and thirdly associated with protozoa or algae.

This test method outlines a method to validate the efficacy of a cooling tower biocide against enzyme treated *Legionella* entrapped in biofllm. The biofilm is removed from cooling tower by scraping the biofilm and re-suspending it in phosphate buffer dilution water. The enzyme formulations are prepared in four 100 mL aliquots and corrosion inhibitor combined with representative anions are added. After 1 hour contact time 1 ml inoculum is added allowed to digest by the enzyme solution for 1 hour and challenged with 1 0ppm isothiazolin and after a contact time of 1 hour. The surviving *Legionella* is determined by plate count method. The test is repeated for enzymes in contact with cooling tower water for 2 hours, 6 hours and 24 hours.

Materials

Petri dish

Incubator 36±1° C.

Pipettes and tips

Vortex mixer

Glassware—

Beakers various sizes, 25 mL universal bottle, 14 mL McCartney bottles

Wide mouth bottles 1L,500 mL

Graduated pipettes 0.1 ml, 1 mL, 5 mL and 10 mL

Syringes various volumes

Class 2 laminar flow cabinet

Filtration unit(eg Sartorius SM 16219 or SM 16517)

0.2 µm filters to fit the filtration unit

Sterile Pasteur pipette packed with cotton wool

Scalpel blade

Glass spreader

McFarland Standard

Buffered Charcoal Yeast Extract Agar(BCYE)

| Oxoid Legionella agar base | 12.5 g |
|---|---|
| Water to | 450 ml |

Suspend 12.5 g in 450 mL distilled water and bring gently to boil to dissolve completely. Distribute in 1 Liter bottle,. Sterilise by autoclaving at 121° C. for 15 minutes. Cool to 50° C. and aseptically add Oxoid BCYE supplement (SR110A) mix gently and pour into sterile petri dish.

Sterile Water for Washing Filter Pads

Distribute distilled water in 10.0 mL volumes in universal wide mouth bottles, autoclave at 121° C. for 15 minutes.

Synthetic Cooling Tower Water.

Prepare 1 L of the solution containing:

200 ppm sulphate ions 200 ppm chloride ions 100 ppm zinc phosphonate

Transfer into 2L glass beaker cover lid with aluminum foil. Sterilise at 121° C. for 20 minutes.

For control dispense 1L Phosphate Buffer dilution water into 2L glass beaker cover lid with aluminum foil sterilise at 121° C. for 20 minutes.

Phosphate Buffer Stock Solution Water

Dissolve 34.0 g $KH_2PO_4$ in 500 ml distilled water, adjust pH to 7.2 with 1 N NaOH and dilute to 1L.

Phosphate Buffer Dilution Water

Add 1.25 mL Phosphate buffer stock solution to 1L distilled water. Distribute in 9 mL quantities in McCartney bottles and sterilise at 121° C. for 20 minutes.

Test Organism

Legionella pneumophilia (NCTC 11404)

From a laboratory cooling tower set up grow Legionella. Carefully scrape the biofilm from the substratum. Suspend in phosphate buffered water. Use this for challenging the enzyme solution.

Operating Technique

The following enzyme formulations were tested

| T1 | |
|---|---|
| Alcalase 2.5DXL | 20 |
| Thermamyl 300DX | 20 |
| Propylene Glycol | 16 |
| Borax | 4.5 |
| Glycerol | 4 |
| Water | QC |

T2:—Non formulated enzyme

Into a set of eight 125 ml sterile sample containers add 100 mL sterile distilled water to each container.

Label each container.

The first four containers are used for T1 and the other four for T2.

T1,1—T1 after 1 hour digestion
T1,2—T1 after 4 hour digestion
T1,6—T1 after 6 hour digestion
T1,24—T1 after 24 hour digestion
T2,1—T2 after 1 hour digestion
T2,2—T2 after 4 hour digestion
T2,6—T2 after 6 hour digestion
T2,24—T2 after 24 hour digestion Add enzyme compositions to be tested to each container to achieve concentrations of 2.5xE-3 Au/g protease and 300 Nu/g amylase formulation in each of container.

Add 100 ppm zinc phosphonate corrosion inhibitor

Start timer.

At the following time intervals

At 1 hour add 1 mL of *Legionella* suspension to container labelled T1,1 and T2,1

Immediately remove 10 mL suspension for *Legionella* plate count(before treatment).

Digest for 1 hour. After 1 hour digestion add 10 ppm of isothiazolin and allow to stand for further 1 hour.

Remove 10 mL suspension for *Legionella* plate count (after treatment).

At 4 hours repeat the above test with treatments labelled T1,2 and T2,2

At 6 hours repeat the above test with treatments labelled T1,6 and T2,6

At 24 hours repeat the above test with treatments labelled T1,24 and T2,24

*Legionella* Plate Count

For each sample obtained carry out the following procedure.

Filter the 10 mL sample through 0.22 μm filter

Wash filter with 10 mL sterile water to flush any biocidal residues.

Aseptically remove filter pad chop into pieces using a flamed scalpel blade and suspend in 10 mL sterile distilled water.

Vortex for 30 sec. to bring surviving cells into suspension.

Prepare a series of ten fold dilutions in 9 mL sterile distilled water

For before treatment samples transfer 0.1 mL from $10^{-4}$ and $10^{-3}$ and $10^{-2}$ dilutions into BCYE agar plates in duplicate.

For after treatment samples transfer 0.1 mL from $10^{-4}$, $10^{-3}$, $10^{-2}$ and $10^{-1}$ dilutions into BCYE agar plates in duplicate.

Calculations

Count the colonies on plates containing between 25 and 250.

The surviving *Legionella* can be calculated from before and after treatment count and converted into log The claims defining the invention are as follows:

1. A method of treating sessile micro-organisms in a biofilm in a water system, said method comprising adding to the system an effective amount of at least one planktonising enzyme and an enzyme-conditioning amount of at least one boron compound wherein enzyme activity two hours after adding the at least one boron compound is at least 40% of enzyme activity prior to adding the at least one boron compound and wherein the at least one enzyme and the at least one boron compound are synergistically effective in combination.

2. A method of planktonising sessile micro-organisms in a biofilm, said method comprising adding an effective amount of at least one planktonising enzyme to a water system in contact with the biofilm, and an enzyme-conditioning amount of at least one boron compound wherein enzyme activity two hours after adding the at least one boron compound is at least 40% of enzyme activity prior to adding the at least one boron compound, and wherein the at least one enzyme and the at least one boron compound are synergistically effective in combination.

3. A method according to claim 1, further comprising adding an effective amount of at least one biocide; and wherein enzyme activity two hours after the latter of the adding of the at least one planktonising enzyme and the adding of the at least one biocide is at least 40% of enzyme activity prior to the latter of the adding of the at least one planktonising enzyme and the adding of the at least one biocide.

4. A method according to claim 1, wherein the water system is a recirculating water system comprising a biofilm, wherein the sessile microorganisms are comprised by the biofilm.

5. A method according to claim 1, wherein the water system temperature is between 40° C. and 55° C. and comprises a biofilm, wherein the sessile microorganisms are comprised by the biofilm.

6. A method according to claim 1, wherein enzyme activity 12 hours after the adding the at least one boron compound is at least 40% of enzyme activity prior to the adding the at least one boron compound.

7. A method according to claim 1, wherein enzyme activity 24 hours after the adding the at least one boron compound is at least 75% of enzyme activity prior to the adding the at least one boron compound.

8. A method according to claim 1, wherein said at least one planktonising enzyme and said at least one boron compound are contacted prior to their addition to the water.

9. A method according to claim 1, wherein said at least one boron compound and said at least one planktonising enzyme are contacted in the water system.

10. A method according to claim 3, wherein said at least one planktonising enzyme, said at least one boron compound and said at least one biocide are added to the water system substantially continuously.

11. A method according to claim 3, wherein at least one of said at least one planktonising enzyme and said at least one biocide is added to the water system intermittently.

12. A method according to claim 1, wherein said at least one planktonising enzyme is selected from the group consisting of a protease, a carbohydrase, an esterase, a hydraze, an amylase, a catalase, a lipase, a cellulose, a peroxidase, an invertase, a levanbiohydrolase and a mixture thereof.

13. A method according to claim 12, wherein said at least one planktonising enzyme is a protease, an amylase or a mixture thereof.

14. A method according to claim 1, wherein said at least one enzyme is a protease employed at an activity of 1 E-3 to 3E-3 Au/g.

15. A method according to claim 1, wherein said at least one planktonising enzyme is an amylase employed in a concentration equivalent to 100-500 Nu/g.

16. A method according to claim 1, wherein said at least one boron compound is selected from the group consisting of borax, boric acid, boric oxides, ortho-borates, meta-borates pyro-borates, perborates, boronic acids and a mixture thereof.

17. A method according to claim 1, wherein said at least one boron compound is added to a concentration of 0.1 to 10%.

18. A method according to any one claim 3, wherein the at least one biocide is selected from the group consisting of a thiazole/imidazole biocide, a nitroparaffin biocide, a thiadiazine, a dithiocarbamate, a thiocyanate, a quaternary ammonium chloride and a mixture thereof.

19. A method according claim 3, wherein said at least one biocide is in a concentration of from 1 to 150 ppm.

20. A method according to claim 1, wherein said water system includes at least one corrosion inhibitor.

21. A method according claim 20 wherein the at least one corrosion inhibitor is selected from the group consisting of an oxidising corrosion inhibitor and a film forming corrosion inhibitor.

22. A method according claim 1, wherein planktonic and sessile bacteria in total in said water are maintained at below 1000 cfu/ml.

23. A method according to claim 1, wherein planktonic and sessile bacteria in total in said water system are maintained at below 10 cfu/ml.

24. A method according to claim 3, wherein said treating sessile micro-organisms comprises reducing growth of the planktonic and sessile micro-organisms, and wherein the planktonic and sessile micro-organisms comprise at least one micro-organism selected from the group consisting of a *Legionella* micro-organism, *Aerobacter levanicum*, *Pseudomonas aeruginosa*, a *Rhodoturula glutinis* yeast, and *Bacillus subtilis*.

25. A method according to claim 24 wherein said reducing growth of the planktonic and sessile microorganisms comprises reducing growth of a *Legionella* micro-organism.

26. A method of treatment of water comprising:
providing at least one enzyme having an initial activity in water;
conditioning said enzyme with a sufficient concentration of a boron compound to produce a boron conditioned enzyme; and
adding at least one biocide
wherein when said boron conditioned enzyme is in contact with said water it retains a level of activity at least 40% of said initial activity for at least two hours after contacting said water, and wherein the at least one enzyme and the at least one biocide are synergistically effective in combination.

27. A method of remediating a tepid water system harbouring micro-organisms, the method comprising:
introducing to the system at least one enzyme having an initial activity in water; and
conditioning said enzyme with a sufficient concentration of a boron compound to produce a boron conditioned enzyme
wherein said boron conditioned enzyme retains a level of activity at least 40% of said initial activity for at least two hours after said introducing, and wherein the at least one enzyme and the at least one boron compound are synergistically effective in combination.

28. A method according to claim 27 wherein the tepid water is between 40° C. and 55° C.

29. A method according to claim 28, wherein the tepid water is between 45° C. and 50° C.

30. A composition for treating water, the composition comprising:
   at least one enzyme having an initial activity;
   a sufficient amount of at least one boron compound to condition and stabilise said enzyme so as to form a boron conditioned enzyme; and
   at least one biocide
wherein the boron conditioned enzyme retains at least 40% of the initial activity for at least two hours after contacting the water and wherein the enzyme and the biocide are synergistically effective in combination.

31. A composition according to claim 30, wherein said enzyme is selected from the group consisting of a protease, a carbohydrase, an esterase, a hydraze, an amylase, a catalase, a lipase, a cellulase, a peroxidase, an invertase, a levanbiohydrolase and a mixture thereof.

32. A composition according to claim 30, wherein said at least one enzyme is a protease, an amylase or a mixture thereof.

33. A composition according to claim 32, wherein said protease provides an activity of at least 1E-3 to 3E-3Au/g when added to said water.

34. A composition according to claim 32, wherein said amylase provides an activity of 100-500 Nu/g when added to said water.

35. A composition according claim 30, wherein said at least one boron compound is selected from the group consisting of borax, boric acid, a boric oxide, an orthoborate, a meta borate, a pyroborate, a perborate, a boronic acid and a mixture thereof.

36. A composition according to claim 30, wherein said boron compound is present in a concentration of 0.1 to 10%.

37. A composition according to claim 30, further comprising at least one micelle-immiscible solvent.

38. A composition according to claim 37, wherein the at least one micelle-immiscible solvent is a polyol selected from the group consisting of glycerol, propylene glycol, and a mixture thereof.

39. A composition according to claim 30, wherein said at least one biocide is selected from the group consisting of a thiazole/imidazole a nitroparaffin biocide, a thiadiazine, a dithiocarbamate, a thiocyanate, a quaternary ammonium chloride and a mixture thereof.

40. A composition according to claim 30, wherein said at least one biocide provides a concentration of from 1 to 10% when added to said water.

41. A composition according to claim 30, further including a corrosion inhibitor.

* * * * *